(12) United States Patent
Derenne et al.

(10) Patent No.: US 11,013,650 B2
(45) Date of Patent: May 25, 2021

(54) PATIENT TRANSPORT APPARATUS WITH MOVABLE HEAD SECTION

(71) Applicant: Stryker Corporation, Kalamazoo, MI (US)

(72) Inventors: Richard A. Derenne, Portage, MI (US); Kurosh Nahavandi, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 355 days.

(21) Appl. No.: 16/210,867

(22) Filed: Dec. 5, 2018

(65) Prior Publication Data

US 2019/0183702 A1     Jun. 20, 2019

Related U.S. Application Data

(60) Provisional application No. 62/607,600, filed on Dec. 19, 2017.

(51) Int. Cl.
*A61G 7/018*      (2006.01)
*A61G 7/08*      (2006.01)
(Continued)

(52) U.S. Cl.
CPC ............ *A61G 7/018* (2013.01); *A47C 19/022* (2013.01); *A47C 19/04* (2013.01); *A61G 7/005* (2013.01);
(Continued)

(58) Field of Classification Search
CPC ........ A61G 7/018; A61G 7/005; A61G 7/002; A61G 7/015; A61G 7/0506; A61G 7/05;
(Continued)

(56) References Cited

U.S. PATENT DOCUMENTS

| | | | | | |
|---|---|---|---|---|---|
| 272,077 A | * | 2/1883 | Mueller | ............... | A47C 19/04 5/183 |
| 402,129 A | * | 4/1889 | Beckert | ............... | A47C 19/04 5/183 |

(Continued)

FOREIGN PATENT DOCUMENTS

| | | |
|---|---|---|
| AT | 226411 T | 11/2002 |
| AT | 463224 T | 4/2010 |

(Continued)

OTHER PUBLICATIONS

English language abstract for AT 226411 extracted from espacenet.com database on Feb. 13, 2019, 2 pages.
(Continued)

*Primary Examiner* — Robert G Santos
(74) *Attorney, Agent, or Firm* — Howard & Howard Attorneys PLLC

(57) ABSTRACT

A patient transport apparatus comprises support structure. The support structure comprises a base, a support frame, and a patient support deck. A headboard and a footboard are coupled to the support structure. The support frame comprises a head section and a body section, the body section coupled to the patient support deck. The patient support deck comprises a patient support surface capable of articulating relative to the support frame. The head section is movable relative to the body section to define first and second configurations of the support frame, the support frame having a first footprint in the first configuration and a second footprint, smaller than the first footprint, in the second configuration.

20 Claims, 8 Drawing Sheets

(51) Int. Cl.
*A61G 7/10* (2006.01)
*A61G 7/05* (2006.01)
*A61G 7/005* (2006.01)
*A61G 7/015* (2006.01)
*A47C 19/04* (2006.01)
*A47C 19/02* (2006.01)
*A61B 5/00* (2006.01)

(52) U.S. Cl.
CPC ........... *A61G 7/015* (2013.01); *A61G 7/0506* (2013.01); *A61G 7/08* (2013.01); *A61G 7/1013* (2013.01); *A61B 5/6892* (2013.01); *A61B 2562/0252* (2013.01); *A61G 7/0528* (2016.11); *A61G 7/1046* (2013.01); *A61G 7/1067* (2013.01); *A61G 2203/32* (2013.01)

(58) Field of Classification Search
CPC ........ A61G 7/08; A61G 7/1013; A47C 19/04; A47C 19/02; A47C 19/021; A47C 19/022
USPC .............................. 5/613, 616, 617, 181, 183
See application file for complete search history.

(56) References Cited

U.S. PATENT DOCUMENTS

| | | | |
|---|---|---|---|
| 1,004,243 A * | 9/1911 | Cooper | A47C 19/04 5/183 |
| 1,259,022 A * | 3/1918 | Kean et al. | A47C 19/04 5/183 |
| 1,394,331 A * | 10/1921 | Monroe | A47C 19/04 5/183 |
| 1,394,985 A * | 10/1921 | Fischer | A47C 20/043 5/617 |
| 2,611,907 A * | 9/1952 | Clerc | A47C 19/124 5/176.1 |
| 2,739,319 A * | 3/1956 | Keller | A47C 20/043 5/617 |
| 3,335,432 A * | 8/1967 | Foster | A47C 17/12 5/617 |
| 3,673,765 A | 7/1972 | Dohmeier et al. | |
| 4,679,261 A * | 7/1987 | Stanley | A47C 19/04 403/104 |
| 4,724,555 A * | 2/1988 | Poehner | A61G 7/0506 5/183 |
| 5,745,937 A | 5/1998 | Weismiller et al. | |
| 6,021,533 A | 2/2000 | Ellis et al. | |
| 6,071,579 A | 6/2000 | Green et al. | |
| 6,076,208 A * | 6/2000 | Heimbrock | A61G 7/00 5/183 |
| 6,115,337 A | 9/2000 | Takagi et al. | |
| 6,202,231 B1 * | 3/2001 | Heimbrock | A61G 7/00 5/181 |
| 6,295,675 B1 | 10/2001 | Ellis et al. | |
| 6,357,065 B1 | 3/2002 | Adams | |
| 6,467,113 B2 | 10/2002 | Ellis et al. | |
| 6,760,939 B2 | 7/2004 | Ellis et al. | |
| 6,836,912 B1 * | 1/2005 | Morris | A47C 19/04 5/181 |
| 7,028,358 B2 | 4/2006 | Liu | |
| 7,111,348 B2 | 9/2006 | Ellis et al. | |
| 7,260,860 B2 | 8/2007 | Chambers et al. | |
| 7,353,556 B2 | 4/2008 | Ellis et al. | |
| 7,363,663 B2 | 4/2008 | Chambers et al. | |
| 7,398,573 B2 | 7/2008 | Ellis et al. | |
| 7,461,425 B2 | 12/2008 | Chambers et al. | |
| 7,464,425 B2 | 12/2008 | Chambers et al. | |
| 7,565,710 B2 | 7/2009 | Chambers et al. | |
| 7,832,039 B2 | 11/2010 | Chambers et al. | |
| 7,845,032 B2 | 12/2010 | Chambers et al. | |
| 8,104,122 B2 | 1/2012 | Richards et al. | |
| 8,122,546 B2 | 2/2012 | Chambers et al. | |
| 8,650,686 B2 | 2/2014 | Biggie et al. | |
| 9,149,400 B2 | 10/2015 | Serhan | |
| 9,381,125 B2 * | 7/2016 | Herbst | A61G 7/0528 |
| 10,470,582 B2 * | 11/2019 | Odutayo | A47C 7/002 |
| 2002/0029423 A1 | 3/2002 | Ellis et al. | |
| 2003/0019042 A1 | 1/2003 | Ellis et al. | |
| 2004/0261185 A1 | 12/2004 | Ellis et al. | |
| 2006/0026767 A1 | 2/2006 | Chambers et al. | |
| 2006/0026768 A1 | 2/2006 | Chambers et al. | |
| 2006/0075558 A1 | 4/2006 | Lambarth et al. | |
| 2007/0011817 A1 | 1/2007 | Ellis et al. | |
| 2007/0017032 A1 | 1/2007 | Ellis et al. | |
| 2007/0136949 A1 | 6/2007 | Richards et al. | |
| 2008/0005847 A1 | 1/2008 | Chambers et al. | |
| 2008/0005848 A1 | 1/2008 | Chambers et al. | |
| 2008/0010752 A1 | 1/2008 | Chambers et al. | |
| 2009/0070942 A1 | 3/2009 | Chambers et al. | |
| 2009/0249552 A1 | 10/2009 | Chambers et al. | |
| 2010/0257672 A1 | 10/2010 | Poulos et al. | |
| 2011/0047709 A1 | 3/2011 | Tarsaud et al. | |
| 2011/0099723 A1 | 5/2011 | Chambers et al. | |
| 2011/0232001 A1 | 9/2011 | Poulos et al. | |
| 2013/0227787 A1 * | 9/2013 | Herbst | A61G 7/0509 5/611 |
| 2014/0026325 A1 | 1/2014 | Guthrie | |
| 2014/0047641 A1 | 2/2014 | Thodupunuri et al. | |
| 2015/0128347 A1 | 5/2015 | Hutchison et al. | |
| 2016/0302985 A1 | 10/2016 | Tessmer et al. | |
| 2017/0172829 A1 | 6/2017 | Tessmer et al. | |
| 2017/0246065 A1 | 8/2017 | Connell et al. | |
| 2018/0055237 A1 * | 3/2018 | Odutayo | A47C 19/04 |
| 2018/0360681 A1 | 12/2018 | Paul | |
| 2019/0183702 A1 * | 6/2019 | Derenne | A61G 7/1013 |

FOREIGN PATENT DOCUMENTS

| | | |
|---|---|---|
| AU | 8503598 A | 3/1999 |
| AU | 8292998 A | 8/1999 |
| BR | 9811375 A | 8/2000 |
| CA | 2301609 A1 | 3/1999 |
| CA | 2505097 A1 | 9/2006 |
| CA | 2505101 A1 | 9/2006 |
| DE | 69808941 T2 | 2/2003 |
| EP | 1011391 A1 | 6/2000 |
| EP | 1234565 A2 | 8/2002 |
| EP | 1011391 B1 | 10/2002 |
| EP | 1234565 A3 | 12/2002 |
| EP | 1234565 B1 | 4/2010 |
| EP | 2698137 A1 | 2/2014 |
| EP | 2289477 B1 | 9/2014 |
| EP | 2877058 A1 | 6/2015 |
| EP | 2954884 A1 | 12/2015 |
| EP | 3058923 A1 | 8/2016 |
| EP | 2954884 B1 | 4/2018 |
| JP | 2001513384 A | 9/2001 |
| JP | 2016028675 A | 3/2016 |
| TW | 279228 B | 6/1996 |
| TW | 404829 B | 9/2000 |
| WO | 9909865 A1 | 3/1999 |
| WO | 9941537 A1 | 8/1999 |
| WO | 2014018758 A1 | 1/2014 |
| WO | 2014201379 A2 | 12/2014 |
| WO | 2014201379 A3 | 2/2015 |

OTHER PUBLICATIONS

English language abstract for AT 463224 extracted from espacenet.com database on Feb. 13, 2019, 2 pages.
English language abstract for AU 8503598 extracted from espacenet.com database on Feb. 13, 2019, 2 pages.
English language abstract for AU 8292998 extracted from espacenet.com database on Feb. 13, 2019, 2 pages.
English language abstract for BR 9811375 extracted from espacenet.com database on Feb. 13, 2019, 2 pages.
English language abstract for DE 69 808 941 extracted from espacenet.com database on Feb. 13, 2019, 2 pages.
English language abstract for JP 2001-513384 extracted from espacenet.com database on Feb. 13, 2019, 2 pages.
English language abstract for JP 2016-028675 extracted from espacenet.com database on Feb. 13, 2019, 2 pages.

(56) References Cited

OTHER PUBLICATIONS

English language abstract for TW 279228 extracted from espacenet.com database on Feb. 13, 2019, 2 pages.
English language abstract for TW404826 extracted from espacenet.com database on Feb. 13, 2019, 2 pages.

* cited by examiner

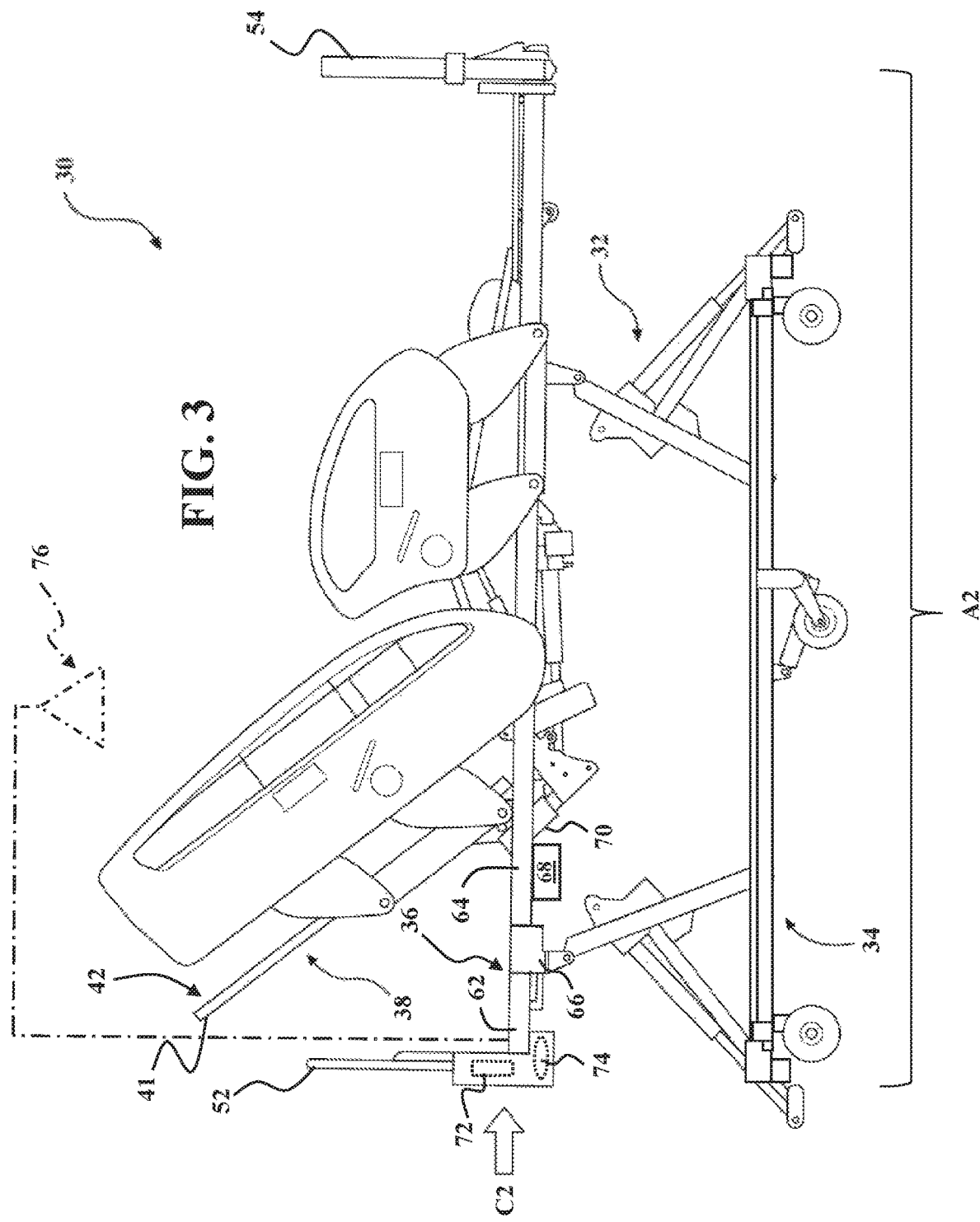

PATIENT TRANSPORT APPARATUS WITH MOVABLE HEAD SECTION

CROSS-REFERENCE TO RELATED APPLICATION

The subject patent application claims priority to and all the benefits of U.S. Provisional Patent Application No. 62/607,600 filed on Dec. 19, 2017, the disclosure of which is hereby incorporated by reference in its entirety.

BACKGROUND

Patient transport systems facilitate care of patients in a health care setting. Patient transport systems comprise patient transport apparatuses (e.g., beds, stretchers, cots, recliners, wheelchairs, etc.) to move patients between locations. Patient transport apparatuses comprise a support structure having a support frame carrying a patient support deck upon which the patient is supported, and an articulation system for articulating one or more sections of the patient support deck relative to the support frame.

Sometimes, it is desirable to configure the support frame and the patient support deck to create a smaller footprint of the patient transport apparatus. These configurations may prevent contact between the patient transport apparatus and an obstruction. For example, an obstruction may be encountered when the patient transport apparatus is being moved into a smaller space (e.g., a small room or elevator). In some cases, when placing the patient transport apparatus in such desirable configurations, obstacles can cause damage to the patient transport apparatus or harm the patient.

A patient transport apparatus is desired that addresses one or more of the aforementioned challenges.

BRIEF DESCRIPTION OF THE DRAWINGS

FIG. 3 is an illustration of the patient transport apparatus with the headboard and the head section transitioning from the first configuration into a second configuration.

DETAILED DESCRIPTION

Figure 1:
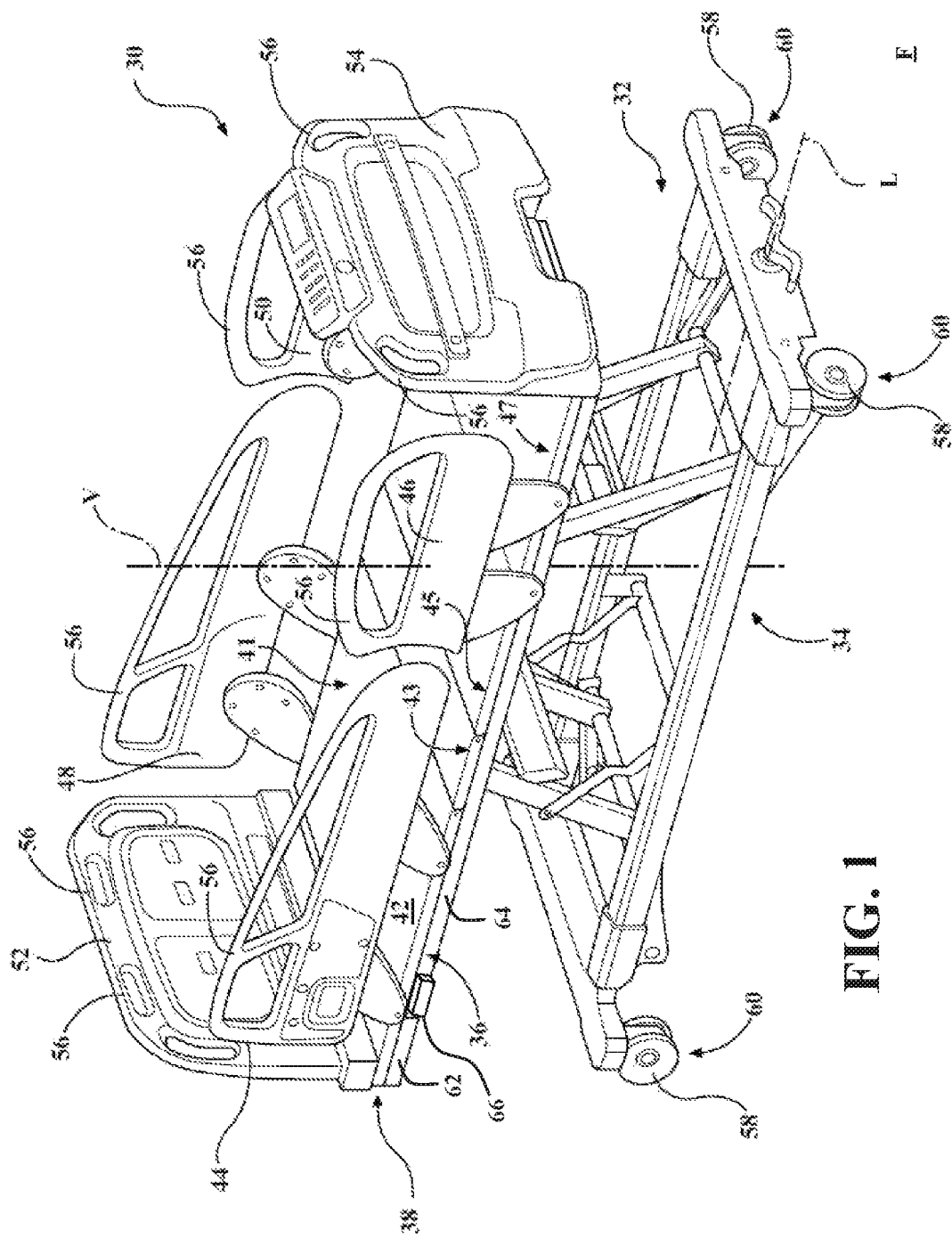
FIG. 1 is perspective view of a patient transport apparatus.

Referring to FIG. 1, a patient transport apparatus 30 is shown for supporting a patient in a health care setting. The patient transport apparatus 30 illustrated in FIG. 1 comprises a hospital bed. In other embodiments, however, the patient transport apparatus 30 may comprise a stretcher, cot, table, wheelchair, chair, or similar apparatus utilized in the care of a patient.

A support structure 32 provides support for the patient. The support structure 32 illustrated in FIG. 1 comprises a base 34 and a support frame 36. The base 34 comprises a base frame 35. The support frame 36 is spaced above the base frame 35 in FIG. 1. The support structure 32 also comprises a patient support deck 38 disposed on the support frame 36. The patient support deck 38 comprises several sections, some of which are capable of articulating (e.g., pivoting) relative to the support frame 36, such as a back (fowler) section 41, a seat section 43, a leg section 45, and a foot section 47. The patient support deck 38 provides a patient support surface 42 upon which the patient is supported.

A mattress (not shown) is disposed on the patient support deck 38 during use. The mattress comprises a secondary patient support surface upon which the patient is supported. The base 34, support frame 36, patient support deck 38, and patient support surfaces 42 each have a head end and a foot end corresponding to designated placement of the patient's head and feet on the patient transport apparatus 30. The base 34 comprises a longitudinal axis L along its length from the head end to the foot end. The base 34 also comprises a vertical axis V arranged crosswise (e.g., perpendicularly) to the longitudinal axis L along which the support frame 36 is lifted and lowered relative to the base 34. The construction of the support structure 32 may take on any known design, and is not limited to that specifically set forth above. In addition, the mattress may be omitted in certain embodiments, such that the patient rests directly on the patient support surface 42.

Patient barriers, such as side rails 44, 46, 48, 50 are coupled to the support frame 36 and/or patient support deck 38 and are thereby supported by the base 34. A first side rail 44 is positioned at a right head end. A second side rail 46 is positioned at a right foot end. A third side rail 48 is positioned at a left head end. A fourth side rail 50 is positioned at a left foot end. In the embodiment shown, the head end side rails 44, 48 are mounted to the back section 41 for movement with the back section 41. The foot end side rails 46, 50 are mounted to the support frame 36 for movement with the support frame 36. If the patient transport apparatus 30 is a stretcher or a cot, there may be fewer side rails. The side rails 44, 46, 48, 50 are movable relative to the back section 41/support frame 36 to a raised position in which they block ingress and egress into and out of the patient transport apparatus 30, one or more intermediate positions, and a lowered position in which they are not an obstacle to such ingress and egress. In the embodiment shown, the side rails 44, 46, 48, 50 are connected to the back section 41 and/or the support frame 36 by pivotal support arms to form four bar linkages. Such side rails and the manner in which they may be raised/lowered are shown and described in U.S. Patent Application Publication No. 2017/0172829, filed on Dec. 15, 2016 and entitled "Powered Side Rail For A Patient Support Apparatus," hereby incorporated by reference in its entirety.

A headboard 52 and a footboard 54 are coupled to the support frame 36. The headboard 52 and footboard 54 may be coupled to any location on the patient transport apparatus 30, such as the support frame 36 or the base 34. In still other embodiments, the patient transport apparatus 30 does not include the headboard 52 and/or the footboard 54.

Caregiver interfaces 56, such as handles, are shown integrated into the headboard 52, footboard 54, and side rails 44, 46, 48, 50 to facilitate movement of the patient transport apparatus 30 over a floor surface F. Additional caregiver interfaces 56 may be integrated into other components of the patient transport apparatus 30. The caregiver interfaces 56 are graspable by the caregiver to manipulate the patient transport apparatus 30 for movement, to move the side rails 44, 46, 48, 50, and the like.

Other forms of the caregiver interface 56 are also contemplated. The caregiver interface may comprise one or more handles coupled to the support frame 36. The caregiver interface may simply be a surface on the patient transport apparatus 30 upon which the caregiver logically applies force to cause movement of the patient transport apparatus 30 in one or more directions, also referred to as a push location. This may comprise one or more surfaces on the support frame 36 or base 34. This could also comprise one or more surfaces on or adjacent to the headboard 52, footboard 54, and/or side rails 44, 46, 48, 50. In other embodiments, the caregiver interface may comprise separate handles for each hand of the caregiver. For example, the caregiver interface may comprise two handles.

Wheels 58 are coupled to the base 34 to facilitate transport over the floor surface F. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient transport apparatus 30 may comprise four non-powered, non-steerable wheels, along with one or more powered wheels. In some cases, the patient transport apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 60 and contact the floor surface F in the deployed position, they cause two of the caster assemblies 60 to be lifted off the floor surface F thereby shortening a wheel base of the patient transport apparatus 30. A fifth wheel may also be arranged substantially in a center of the base 34.

In the embodiment shown, the support frame 36 comprises a body section 64 and a head section 62. The head section is disposed at the head end of the support structure 32. The body section 64 is coupled to the patient support deck 38. The head section 62 is movable relative to the body section 64 to define various configurations of the support frame 36.

Figure 2:
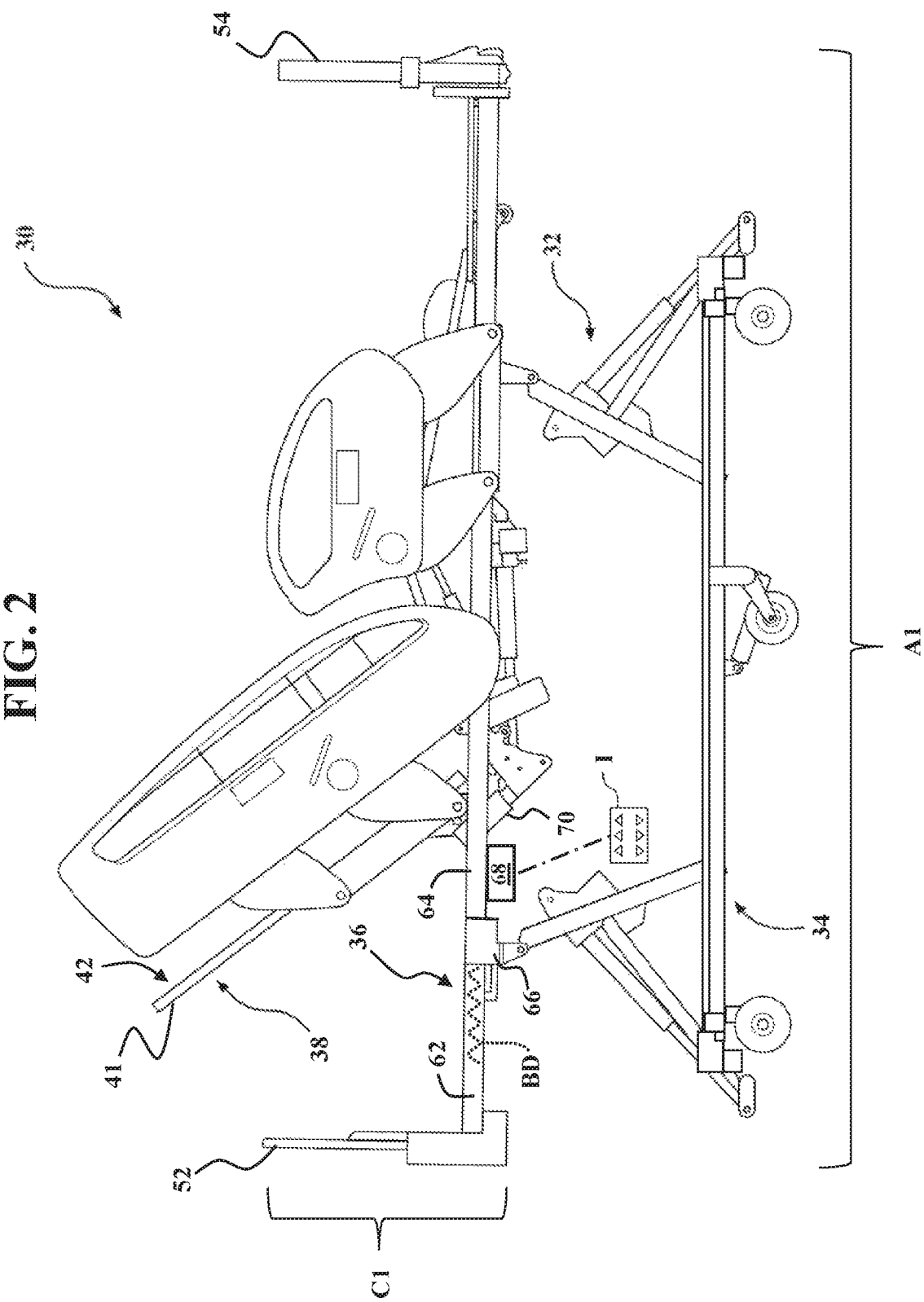
FIG. 2 is a side view of the patient transport apparatus with a headboard and a head section in a first configuration.

Referring to FIG. 2, a side view of the patient transport apparatus 30 is shown in a first configuration C1. The headboard 52 may be vertically arranged such that the headboard 52 is parallel to the vertical axis V when the support frame 36 is horizontally arranged parallel to the longitudinal axis L (see FIG. 1). The support frame 36 has a first footprint A1 in the first configuration C1. In the first configuration C1, the support frame 36 is fully extended, such that the first footprint A1 is the maximum footprint possible for support frame 36. In the first configuration C1, the patient support surface 42 may articulate freely relative to the support frame 36. In other embodiments (not shown), a bed extension device may be located at the foot end of the support structure 32 such that the support frame 36 is further extendable/retractable at the foot end to be configured for taller and shorter patients, respectively. In these embodiments, the first footprint A1 could comprise the bed extension device also being fully extended.

In the embodiment shown, the patient transport apparatus 30 comprises a first actuator 66 coupled to the head section 62 and a controller 68. The first actuator 66 may be operable to retract, extend, and/or articulate the head section 62 relative to the body section 64 to change the configuration of the support frame 36. The patient transport apparatus 30 may further comprise a user input device I coupled to the controller 68 to generate a user input signal. The controller 68 may direct the first actuator 66 to move the head section 62 relative to the body section 64 in response to the user input signal.

In an alternate embodiment, the head section 62 may be operable to be manually articulated relative to the body section 64.

In the embodiment shown, the patient transport apparatus 30 further comprises a second actuator 70 coupled to the patient support deck 38 and the controller 68. The second actuator 70 may be operable to articulate the patient support surface 42 relative to the support frame 36, such as articulating the back section 41 relative to the support frame 36. The actuators 66, 70 may comprise electric actuators, hydraulic actuators, combinations thereof, or any other suitable type of actuators to move the head section 62 and the back section 41. The actuators 66, 70 may be linear actuators, rotary actuators, or combinations thereof.

The controller 68 has one or more microprocessors, microcontrollers, field programmable gate arrays, systems on a chip, discrete circuitry, and/or other suitable hardware, software, or firmware that is capable of carrying out the functions described herein. The controller 68 may be carried on-board the patient transport apparatus 30 (as shown), or may be remotely located. Power to the actuators 66 and 70 and/or the controller 68 may be provided by a battery power supply and/or an external power source. The controller 68 is coupled to the actuators 66 and 70 in a manner that allows the controller 68 to control the actuators 66 and 70. The controller 68 may communicate with the actuators 66 and 70 via wired or wireless connections to perform one of more desired functions. The controller 68 is configured to process instructions or to process algorithms stored in memory to control operation of the actuators 66, 70 to coordinate movement of the actuators 66, 70, which may be simultaneous or sequential, and may be coordinated such that operation of the actuators 66, 70 starts and stops at the same time when both are operating simultaneously.

Referring to FIG. 3, the patient transport apparatus 30 is shown transitioning from the first configuration C1 into a second configuration C2. In transitioning from the first configuration C1 to the second configuration C2, the head section 62 retracts relative to the body section 64. In the second configuration C2, the support frame 36 has a second footprint A2, which is smaller than the first footprint A1. The second footprint A2 may be desirable over the first footprint A1 to avoid collision between the patient transport apparatus 30 and an obstruction B. The obstruction B may be a wall, such as a wall of a room or an elevator, or any other obstacle. In some versions, the base 34 may be configured to also shorten its footprint in a similar manner as the support frame 36 shortens from the first configuration C1 to the second configuration C2.

One possible advantage of placing the support frame 36 into the second configuration C2 is that a range of motion for Trendelenburg movements may be increased by reducing the length of the support frame 36 and thus limiting the potential for contact of the head section 62 with the floor surface F. Furthermore, in patient rooms in which space may be limited, but which may contain multiple patient transport apparatuses 30, the support frame 36 could be moved to the second configuration C2 to provide enough space for another patient transport apparatus 30 to maneuver in the room. Notably, in the movement shown between FIGS. 2 and 3, the support frame 36 shortens when transitioning from the first configuration C1 to the second configuration C2 without affecting the patient support surface 42. As a result, the movement is possible without affecting any patient supported on the patient support surface 42.

In the second configuration C2, articulation of the patient support surface 42 relative to the support frame 36 may be limited because the back section 41, when attempting articulation to a position parallel to support frame 36, may collide with the headboard 52 or the obstruction B. In response to receiving input from a user on the user input device I to operate the second actuator 70 to articulate the back section 41 downward relative to the support frame 36, the controller 68 may direct, in an automated manner, the first actuator 66 to move the head section 62 relative to the body section 64 to change the support frame 36 from the second configuration C2 to the first configuration C1. Additionally, or alternatively, in response to receiving input from a user on the user input device I to operate the first actuator 66 to move the head section 62 relative to the body section 64 to change the support frame 36 from the first configuration C1 to the second configuration C2, the controller 68 may direct, in an automated manner, the second actuator 70 to articulate the back section 41 upward relative to the support frame 36 to avoid a collision between the back section 41 and the headboard 52.

In some embodiments, user feedback devices 72 may be coupled to the controller 68 to indicate a current state of the head section 62, i.e., whether the support frame 36 is in the first configuration C1 or the second configuration C2, and/or to provide feedback to the user to avoid collisions with any obstacles. For instance, in response to the user attempting to operate the first actuator 66 (via the user input device I) to change the support frame 36 from the first configuration C1 to the second configuration C2 when the back section 41 is in a lowered, horizontal position, the controller 68 may generate a signal to actuate one or more of the feedback devices 72 to alert the user of a possible collision condition so that the user is prompted to first raise the back section 41. Likewise, in response to the user attempting to operate the second actuator 70 (via the user input device I) to change the back section 41 from a raised position to the lowered position when the support frame 36 is in the second configuration C2, the controller 68 may generate a signal to actuate one or more of the feedback devices 72 to alert the user of a possible collision condition so that the user is prompted to first change the support frame 36 back to the first configuration C1.

The feedback devices 72 may comprise audible feedback devices (e.g., one or more speakers, piezoelectric devices, etc.), visual feedback devices (e.g., display, LEDs, etc.), and/or tactile feedback devices (e.g., motor with eccentric drive, piezoelectric devices, etc.). The feedback devices 72 may be coupled to the headboard 52, the back section 41, the support frame 36, or on any other suitable location on the patient transport apparatus 30, and/or at remote devices, such as portable electronic devices in communication with the controller 68.

In an embodiment where the head section 62 is translated and/or articulated relative to the body section 64 manually rather than by the actuator 66, the head section 62 may be spring-loaded such that it retracts when it comes in contact with the obstruction B. The head section 62 may automatically extend back to the first configuration C1 when the obstruction B has been cleared. In embodiments in which the head section 62 is translated and/or articulated relative to the body section 64 by the actuator 66, one or more biasing devices BD (e.g., coil springs, leaf springs, gas shock absorbers, oil shock absorbers, etc.) (see hidden lines in FIG. 2) may be located in the head section between the headboard 52 and the actuator 66 to operate in the same manner to retract in response to collisions with any obstructions B.

The patient transport apparatus 30 may further comprise another feedback device 72 configured to indicate a minimum acceptable distance between the patient transport apparatus 30 and the obstruction B when the support frame 36 is in the second configuration C2. The indication of the minimum acceptable distance may be one or more of an audio output, a visual output (e.g., a light projection on a wall surface and/or the floor surface F), and a tactile output. For instance, a light projection could be directed toward the floor surface F to indicate the footprint made by the support frame 36 in the first configuration C1, such as when the support frame 36 is currently in the second configuration C2. This light projection could be made by a light projector coupled to the base 34, the support frame 36, the headboard 52, or to any other suitable location on the patient transport apparatus 30. By way of another example and not limitation, the feedback device 72 may comprise one or more flexible members extending from the support frame 36 to visually represent the length of the support frame 36 in the first configuration C1.

The feedback device 72 may also comprise one or more sensors, audible indicators (e.g., speakers), visual indicators (e.g., display, LEDs, etc.), and tactile indicators (e.g., piezoelectric devices) to indicate the distance needed to be maintained from the headboard 52 to accommodate extension to the first configuration C1, to indicate the current distance, and/or to indicate when the headboard 52 is too close to an obstruction B such that the support frame 36 will be unable to move into the first configuration C1.

The patient transport apparatus 30 may further comprise one or more sensors 74 coupled to the support structure 32 and the controller 68 to sense a position of the head section 62 and/or the back section 41. The sensors 74 may comprise potentiometers, optical sensors, hall-effect sensors, encoders, accelerometers, gyroscopes, inclinometers, etc. The sensors 74 may send signals (by wire or wirelessly) to the controller 68 indicating the position of the head section 62 and/or the back section 41. The controller 68 may limit operation of the second actuator 70 to articulate the back section 41 relative to the support frame 36 based on the position of the head section 62 (e.g., when the support frame 36 is in the second configuration C2) and/or may limit operation of the first actuator 66 to move from the first configuration C1 to the second configuration C2 based on the position of the back section 41.

In some versions, one of the sensors 74 (e.g., a pressure sensor, proximity sensor, or other suitable type of sensor) may be coupled to the controller 68 to detect when the head section 62 is close to the obstruction B or when it contacts the obstruction B, and the controller 68 may be configured to automatically operate the first actuator 66 to retract the head section 62 in response to the head section 62 being within a predefined threshold of the obstruction B or colliding with the obstruction B. This functionality could be deactivated when the user grasps one of the caregiver interfaces 56 (e.g., handles) to push the patient transport apparatus 30. Separate sensors 74 (e.g., capacitive sensors, contact sensors, proximity sensors, etc.) could detect when a user's hand has grasped one of the caregiver interfaces 56 and this would override the automatic retraction function that would otherwise occur if the user were adjacent to the headboard 52.

In some versions, one or more sensors 74 (e.g., accelerometer, speed sensor, etc.) may be used to detect motion and/or speed of the patient transport apparatus 30. In the event motion is detected, the controller 68 may be configured to extend the head section 62 back to the first configuration C1 to give the user enough stride clearance beneath the support frame 36 so that the user's feet are clear of undesirable contact with components of the patient transport apparatus 30 located beneath the support frame 36. For instance, as shown in the embodiment of FIG. 3, when in the second configuration C2, the lift mechanism and the base 34 are located such that it would be difficult for a user to push the patient transport apparatus 30 via the headboard 52 without their feet constantly colliding with the lift mechanism and/or the base. In this case, assuming no other potential collisions are detected, the controller 68, in response to detecting motion (and/or movement above a certain speed threshold) may operate the first actuator 66 to extend the head section 62 to place the support frame 36 back into the first configuration C1 shown in FIG. 2 in which more stride clearance is present for the user.

One of the sensors 74 may also detect a presence of a traction device 76 coupled to the head section 62 and/or to the headboard 52. Movement of the head section 62 when the traction device 76 is coupled to the head section 62 and/or the headboard 52 may be hazardous to the patient. Thus, the sensor 74 may send a signal to the controller 68 indicating that the traction device 76 is coupled to the head section 62 and/or the headboard 52 to prevent the first actuator 66 from moving the head section 62 relative to the body section 64. The sensor 74 may optionally emit a warning signal (e.g., an audio, visual, and/or tactile output) to prevent a user from moving the head section 62 relative to the body section 64 when the traction device 76 is coupled to the head section 62.

Figure 4A:
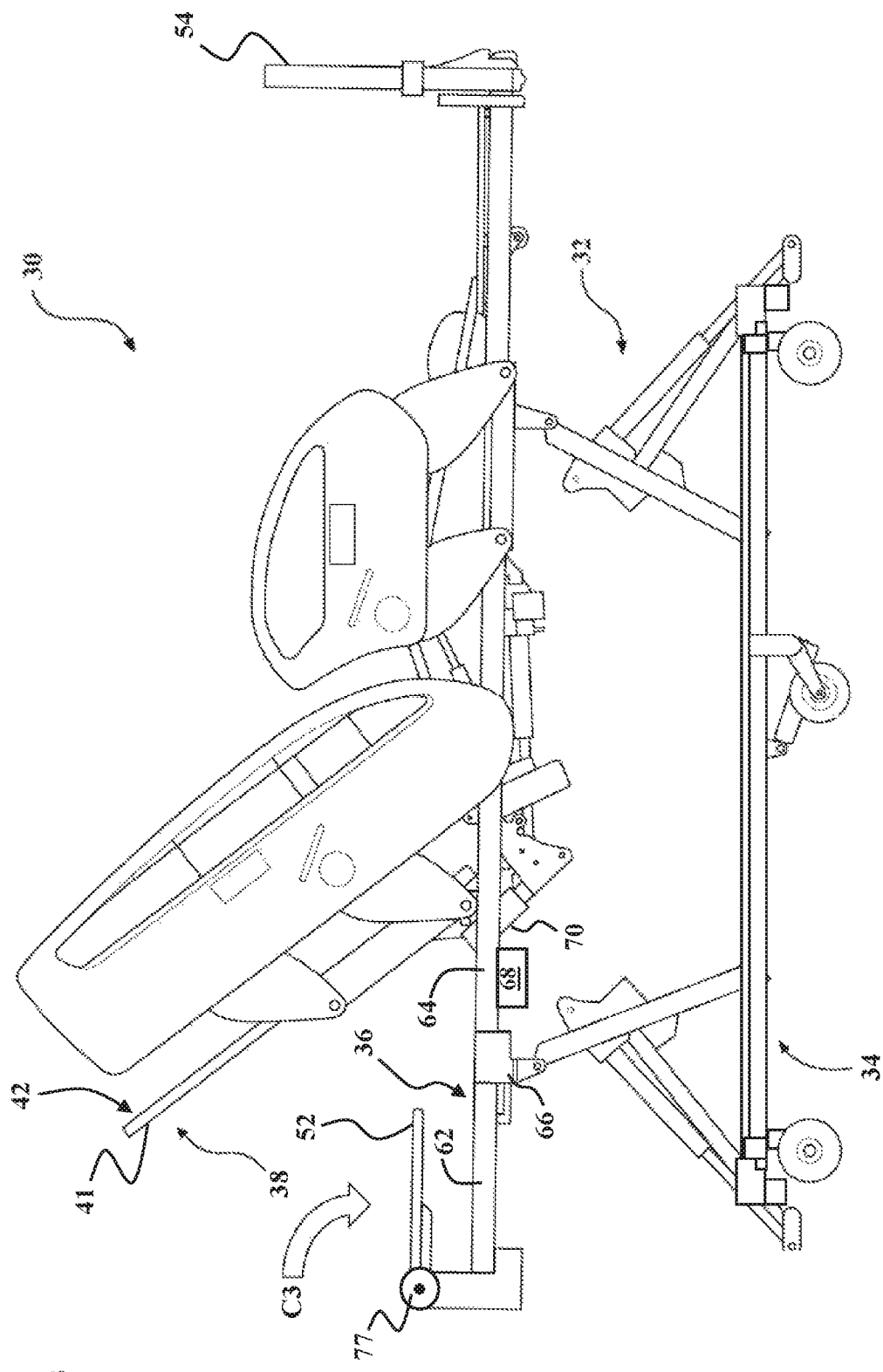
FIG. 4A is an illustration of the patient transport apparatus transitioning from the first configuration into a third configuration.

Referring to FIG. 4A, the patient transport apparatus 30 is shown transitioning from the first configuration C1 into a third configuration C3. The headboard 52 may be carried by the head section 62 and movable with the head section 62 relative to the body section 64. The patient transport apparatus 30 may further comprise a third actuator 77 coupled to the controller 68 and the headboard 52 to move (e.g., pivot about a pivot axis) the headboard 52 relative to the head section 62, or the headboard 52 may be manually operable to articulate relative to the head section 62. The third actuator 77 may comprise an electric actuator, hydraulic actuator, combinations thereof, or any other suitable type of actuator 77 to move the headboard 52. The third actuator 77 may be a linear actuator or rotary actuator (as shown).

The headboard 52 may be movable relative to the head section 62 to avoid contact between the headboard 52 and the back section 41 when the support frame 36 is in the second configuration C2. In the embodiment shown, while the head section 62 is fully extended (i.e., in the first configuration C1), the headboard 52 collapses toward the head section 62 such that the headboard 52 is parallel to the head section 62. The headboard 52 may only partially collapse in other embodiments, and may be spring-biased in some embodiments to collapse automatically in response to collision with the back section 41. The controller 68 operates the third actuator 77 to collapse the headboard 52 in response to the user request on the user input device I, in response to the user requesting movement of the head section 62 from the first configuration C1 to the third configuration C3, and/or in response to the user requesting movement of the head section 62 from the first configuration C1 to a fourth configuration C4 shown in FIG. 4B.

Figure 4B:
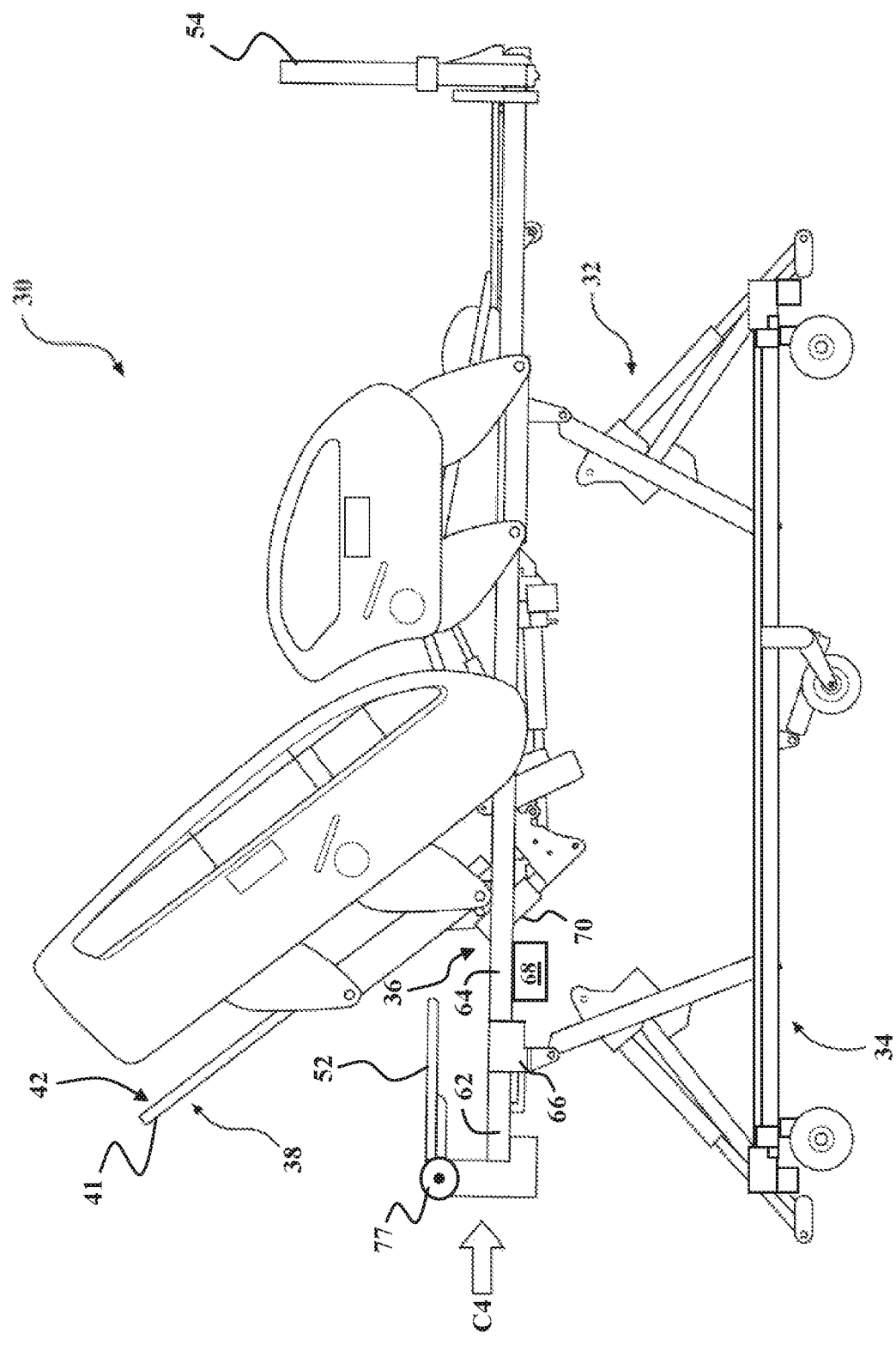
FIG. 4B is an illustration of the patient transport apparatus transitioning from the third configuration into a fourth configuration.

Referring now to FIG. 4B, the patient transport apparatus 30 is shown transitioning from the third configuration C3 into the fourth configuration C4. With the headboard 52 collapsed (or collapsing) toward the headboard 52 such that the headboard 52 is parallel to the head section 62, the head section 62 may retract toward the body section 64 (i.e., into the second configuration C2) to create the fourth configuration C4. Upon the user requesting movement from the first configuration C1 to the fourth configuration C4 (via the user input device I), the controller 68 may first operate the third actuator 77 to collapse the headboard 52 and thereafter operate the first actuator 66 to translate and/or articulate the head section 62 relative to the body section 64 to reduce the footprint of the support frame 36. Alternatively, the third actuator 77 and the first actuator 66 may be simultaneously operated, and their operation may also be coordinated to start and stop at the same time. When returning from the fourth configuration C4 to the first configuration C1, this operation is reversed. The discussion above regarding automated movement of the actuators 66, 70 to avoid collisions similarly applies to the third actuator 77 in this embodiment, i.e., the controller 68 may operate the third actuator 77 in an automated manner to avoid collisions of the headboard 52 with the back section 41.

Figure 4C:
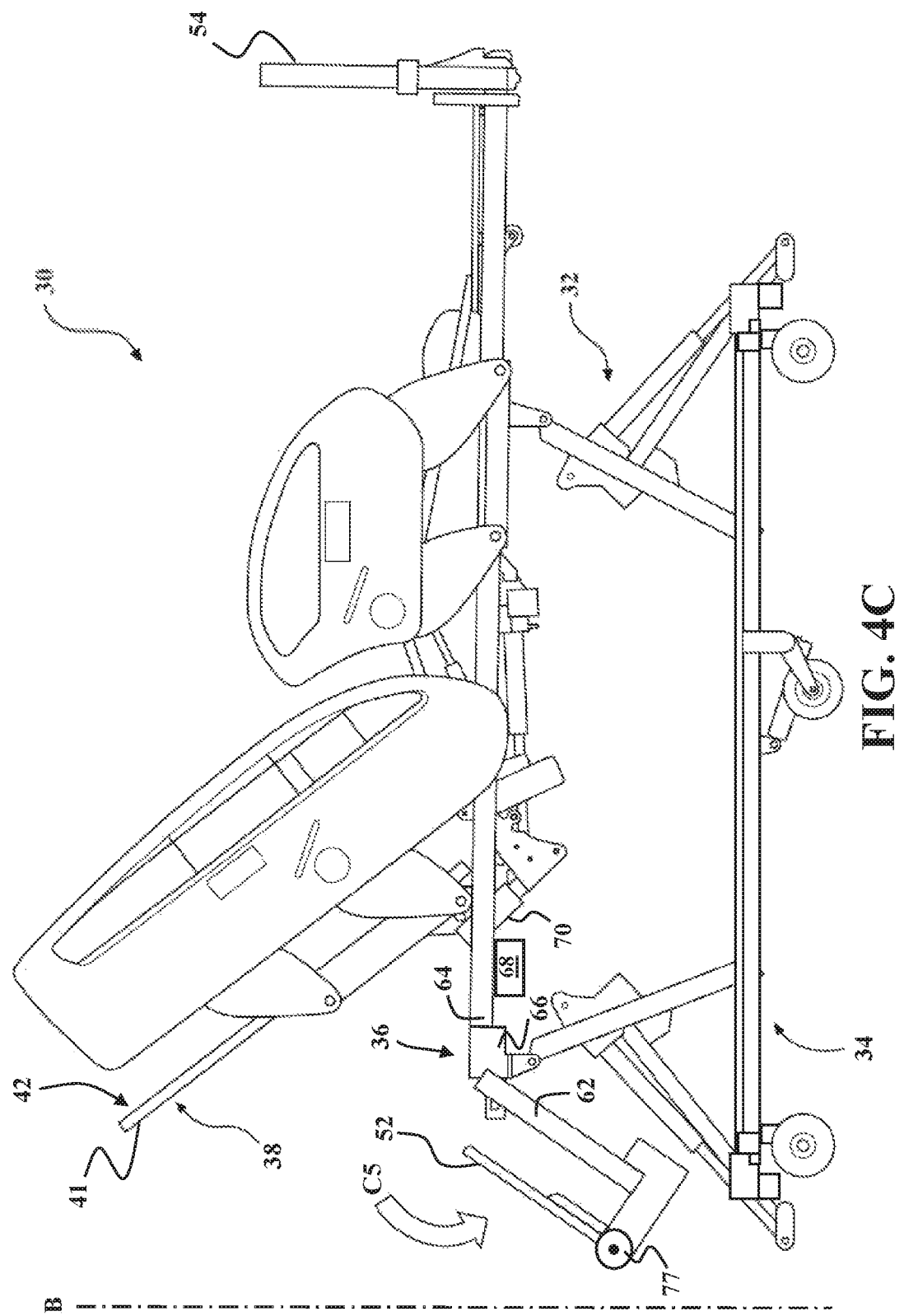
FIG. 4C is an illustration of the patient transport apparatus transitioning from the third configuration into a fifth configuration.

Referring to FIG. 4C, the patient transport apparatus 30 is shown transitioning from the third configuration C3 into a fifth configuration C5. In some conditions, which may be caused by the location of obstruction B and/or the position of the back section 41, it may be preferable to articulate rather than translate the head section 62 relative to the body section 64. With the headboard 52 collapsed toward the head section 62 such that the headboard 52 is parallel to the head section 62, the head section 62 may be articulated downward relative to the body section 64 to create the fifth configuration C5. In this case, the first actuator 66 may be rotary actuator arranged to pivot the head section 62 relative to the body section 64.

Figure 4D:
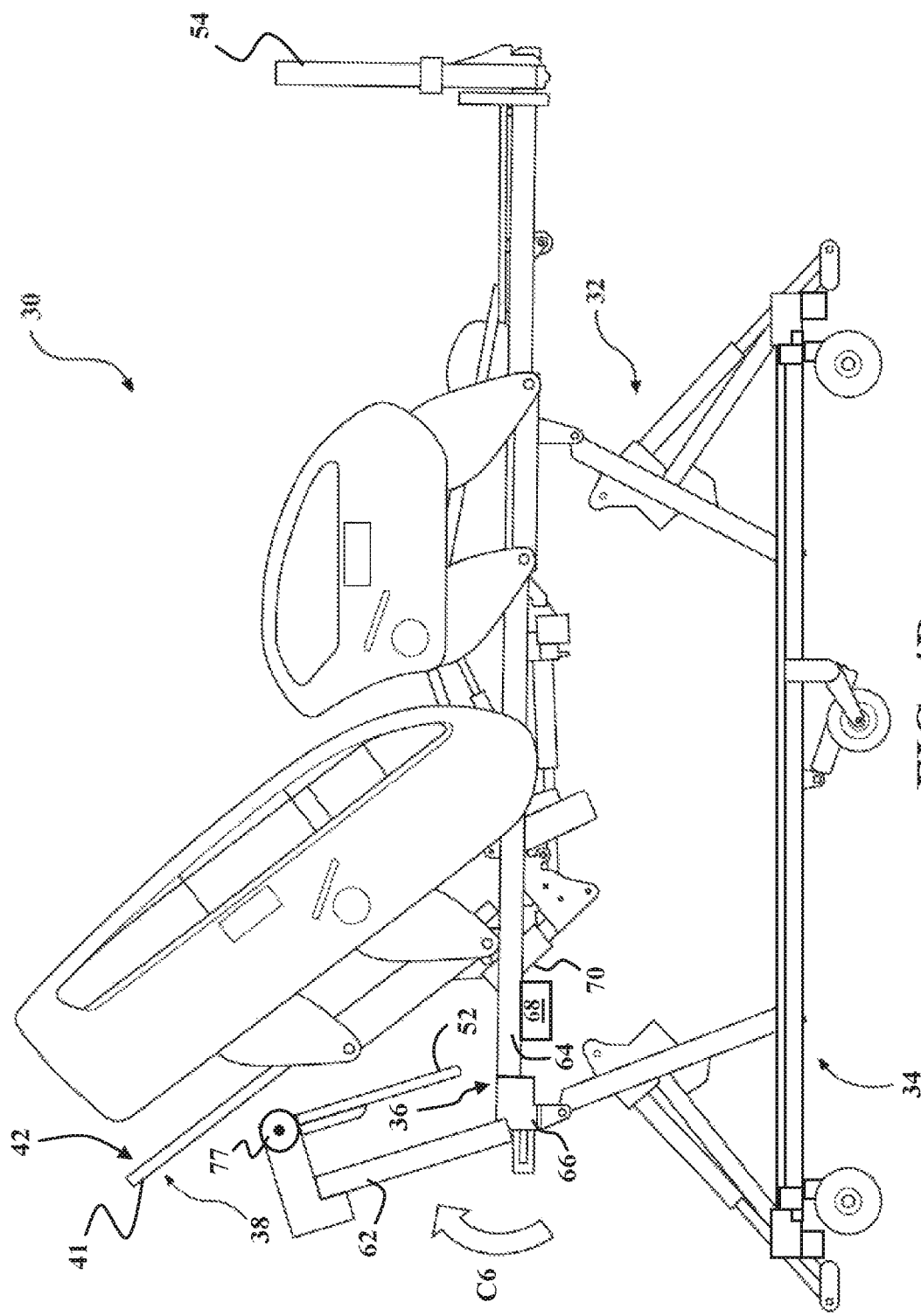
FIG. 4D is an illustration of the patient transport apparatus transitioning from the third configuration into a sixth configuration.

Referring to FIG. 4D, the patient transport apparatus 30 is shown transitioning from the third configuration C3 into a sixth configuration C6. In some conditions, which may be caused by the location of obstruction B and/or the position of the patient support surface 42, it may be preferable to articulate rather than translate the head section 62 relative to the body section 64. With the headboard 52 collapsed toward the head section 62 such that the headboard 52 is parallel to the head section 62, the head section 62 may be articulated upward relative to the body section 64 to create the sixth configuration C6.

Figure 5:
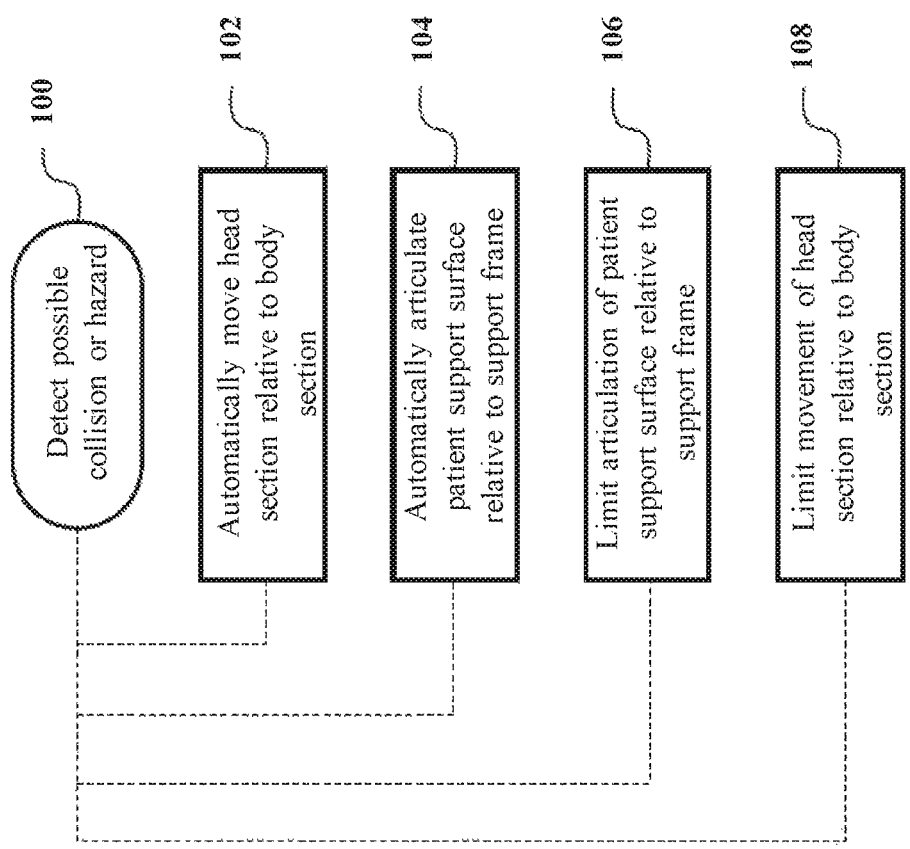
FIG. 5 is a flow diagram of an exemplary method.

Referring to FIG. 5, an exemplary method of controlling movement of the support frame 36 relative to the patient support surface 42 is shown. In step 100, the method starts by first detecting that a collision event or other hazardous condition is possible. This may comprise detecting that the user is moving the head section 62 and/or the headboard 52 while the patient support deck 38 is at a position susceptible to possible collision, or detecting that the user is moving the patient support deck 38 while the head section 62 and/or the headboard 52 is at a position susceptible to possible collision, or detecting that a traction device 74 is coupled to the head section 62 and/or the headboard 52, or the like.

Once the possibility of a collision or other hazardous condition is detected by the controller 68, the method continues to at least one of four actions 102, 104, 106, 108 based on the situation.

In step 102, in response to the second actuator 70 being operated to articulate the back section 41 (and the patient support surface 42) relative to the support frame 36, the controller 68 automatically operates the first actuator 66 to move the head section 62 relative to the body section 64 to change the support frame 36 from the second configuration C2 to the first configuration C1. In some embodiments, the controller 68 may also automatically operate the first actuator 66 to move the head section 62 relative to the body section 64 to change the support frame 36 from the first configuration C1 to the second configuration C2, such as when the second actuator 70 is being operated to raise the back section 41.

In step 104, the controller 68 automatically operates the second actuator 70 to articulate the back section 41 (and the patient support surface 42) relative to the support frame 36, in response to the first actuator 66 being operated to move the head section 62 relative to the body section 64 to change the support frame 36 from the first configuration C1 to the second configuration C2. In some embodiments, the controller 68 may also automatically operate the second actuator 70 to lower the back section 41 relative to the support frame 36, such as when the first actuator 66 is being operated to change the support frame 36 from the second configuration C2 to the first configuration C1.

In step 106, the controller 68 automatically sets a limit on operation of the second actuator 70 to articulate the back section 41 (and the patient support surface 42) relative to the support frame 36 based on the position of the head section 62 and/or the headboard 52, or based on detected distance between the back section 41 (or the patient support surface 42) and the obstruction B, or the like.

In step 108, the controller 68 automatically sets a limit on operation of the first actuator 66 to move the head section 62 relative to the body section 64 based on the position of the back section 41 (and the patient support surface 42) relative to the support frame 36, or based on a detection that the traction device 76 is coupled to the head section 62 and/or the headboard 52, or based on a detected distance between the head section 62 and/or the headboard 52 and the obstruction B, or the like.

In yet another embodiment (not illustrated), the headboard 52 is coupled to the base 34. The base may comprise a structural arm to support headboard 52. The base 34 is movable relative to the body section 64 of the support frame 36 to define first and second configurations of the base 34. The base 34 has a first footprint in the first configuration and a second footprint in the second configuration. In the first configuration, the first footprint of the base 34 is larger than the footprint of the support frame 36. In the second configuration, the second footprint is smaller than the first footprint. It will be appreciated that this embodiment provides the same advantages as the embodiments illustrated in FIGS. 2-4, and may comprise the same mechanisms previously described, the difference being that the footprint of the base 34 is changing instead of the footprint of the support frame 36.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A patient transport apparatus comprising:
a support structure comprising a head end and a foot end, the support structure further comprising:
a base;
a support frame disposed above the base and comprising a body section and a head section, the head section disposed at the head end of the support structure; and
a patient support deck coupled to the body section of the support frame, the patient support deck comprising a patient support surface capable of articulating relative to the support frame to adjust positioning of a patient supported thereon; and
a headboard coupled to the support structure,
wherein the head section of the support frame is movable relative to the body section of the support frame and changes in length to define first and second configurations of the support frame, the support frame having a first footprint in the first configuration and a second footprint, smaller than the first footprint, in the second configuration.

2. The patient transport apparatus of claim 1, further comprising a first actuator coupled to the head section and a controller coupled to the first actuator, the first actuator operable to one or more of retract, extend, and articulate the head section relative to the body section to change the configuration of the support frame.

3. The patient transport apparatus of claim 2, further comprising a second actuator coupled to the patient support deck and the controller, the second actuator operable to articulate the patient support surface relative to the support frame, wherein the controller is configured to direct the first actuator to move the head section relative to the body section to change the support frame from the second configuration to the first configuration in response to the second actuator being operated to articulate the patient support surface relative to the support frame.

4. The patient transport apparatus of claim 2, further comprising a second actuator coupled to the patient support deck and the controller, the second actuator operable to articulate the patient support surface relative to the support frame, wherein the controller is configured to direct the second actuator to move the patient support surface in response to the first actuator being operated to move the head section relative to the body section to change the support frame from the first configuration to the second configuration.

5. The patient transport apparatus of claim 2, further comprising a user input device coupled to the controller to generate a user input signal.

6. The patient transport apparatus of claim 5, wherein the controller is configured to direct the first actuator to move the head section relative to the body section in response to the user input signal.

7. The patient transport apparatus of claim 1, further comprising a feedback device configured to indicate a minimum acceptable distance between the patient transport apparatus and an obstruction when the support frame is in the second configuration;
   wherein the feedback device comprises a flexible member extending from the support frame; and
   wherein the feedback device comprises a sensor.

8. The patient transport apparatus of claim 7, wherein the indication of the minimum acceptable distance by the feedback device comprises one or more of an audio output, a visual output, and a tactile output; and
   wherein the visual output comprises a light projection.

9. The patient transport apparatus of claim 1, wherein the head section is spring-loaded.

10. The patient transport apparatus of claim 1, wherein the head section is operable to be manually moved relative to the body section.

11. The patient transport apparatus of claim 10, further comprising a sensor coupled to the support structure to sense a position of the head section.

12. The patient transport apparatus of claim 11, further comprising an actuator coupled to the patient support deck and a controller coupled to the actuator, the actuator operable to articulate the patient support surface relative to the support frame, wherein the sensor is configured to send a signal to the controller indicating the position of the head section.

13. The patient transport apparatus of claim 12, wherein the controller is configured to limit operation of the actuator to articulate the patient support surface relative to the support frame based on the position of the head section when the support frame is in the second configuration.

14. The patient transport apparatus of claim 2, further comprising a sensor coupled to the controller and configured to detect a presence of a traction device coupled to the head section; and
   wherein the sensor is configured to send a signal to the controller indicating that the traction device is coupled to the head section to prevent the first actuator from moving the head section relative to the body section.

15. The patient transport apparatus of claim 10, further comprising a sensor coupled to the support frame and configured to detect a presence of a traction device coupled to the head section; and
   wherein the sensor is configured to emit a warning signal to prevent a user from moving the head section relative to the body section when the traction device is coupled to the head section.

16. The patient transport apparatus of claim 1, wherein the headboard is coupled to the support frame;
   wherein the headboard is carried by the head section and movable with the head section relative to the body section; and
   wherein the headboard is movable relative to the head section to avoid contact between the headboard and the patient support deck when the support frame is in the second configuration.

17. The patient transport apparatus of claim 16, wherein the headboard is collapsible toward the head section such that the headboard is parallel to the head section when the support frame is in the second configuration.

18. The patient transport apparatus of claim 16, further comprising an actuator coupled to the headboard to move the headboard relative to the head section.

19. A patient transport apparatus comprising:
   a support structure comprising a head end and a foot end, the support structure further comprising:
   a base;
   a support frame disposed above the base and comprising a body section and a head section, the head section disposed at the head end of the support structure; and
   a patient support deck coupled to the body section of the support frame, the patient support deck comprising a patient support surface capable of articulating relative to the support frame to adjust positioning of a patient supported thereon; and
   a headboard carried by the head section and movable with the head section relative to the body section,
   wherein the head section of the support frame is movable relative to the body section and changes in length to define first and second configurations of the support frame, the support frame having a first footprint in the first configuration and a second footprint, smaller than the first footprint, in the second configuration.

20. A patient transport apparatus comprising:
   a support structure comprising a head end and a foot end, the support structure further comprising:
   a base;
   a support frame disposed above the base and comprising a body section and a head section, the head section disposed at the head end of the support structure; and
   a patient support deck coupled to the body section of the support frame, the patient support deck comprising a patient support surface capable of articulating relative to the support frame to adjust positioning of a patient supported thereon,
   wherein the head section of the support frame is movable relative to the body section to define first and second configurations of the support frame, the support frame having a first footprint in the first configuration and a second footprint, smaller than the first footprint, in the second configuration; and
   a first actuator operable to move the head section relative to the body section;
   a second actuator operable to move the patient support surface relative to the support frame; and
   a controller coupled to the first actuator and the second actuator and configured to coordinate operation of the first actuator and the second actuator to move the head section and the patient support surface to prevent contact between the head section and the patient support deck when changing the support frame from the first configuration to the second configuration.

* * * * *